(12) United States Patent
Black

(10) Patent No.: US 7,674,618 B2
(45) Date of Patent: Mar. 9, 2010

(54) EXPRESSION VECTOR

(75) Inventor: Amelia Black, Los Gatos, CA (US)

(73) Assignee: Medarex, Inc., Princeton, NJ (US)

( * ) Notice: Subject to any disclaimer, the term of this patent is extended or adjusted under 35 U.S.C. 154(b) by 490 days.

(21) Appl. No.: 10/934,304

(22) Filed: Sep. 3, 2004

(65) Prior Publication Data

US 2005/0153394 A1 Jul. 14, 2005

Related U.S. Application Data

(60) Provisional application No. 60/500,803, filed on Sep. 4, 2003.

(51) Int. Cl.
C12N 15/00 (2006.01)
C12N 15/10 (2006.01)
C12N 16/65 (2006.01)
C12N 15/79 (2006.01)

(52) U.S. Cl. .................. 435/320.1; 536/24.1; 536/23.1; 536/23.2; 435/69.1; 435/325

(58) Field of Classification Search ....................... None
See application file for complete search history.

(56) References Cited

U.S. PATENT DOCUMENTS

| | | | |
|---|---|---|---|
| 4,713,339 A | 12/1987 | Levinson et al. | |
| 5,256,568 A * | 10/1993 | Panayotatos | 435/252.33 |
| 5,627,033 A * | 5/1997 | Smith et al. | 435/6 |
| 5,629,203 A | 5/1997 | Shuster | |
| RE35,749 E | 3/1998 | Rosenberg et al. | |
| 5,733,779 A | 3/1998 | Reff | |
| 6,017,733 A * | 1/2000 | Reff | 435/69.6 |
| 6,042,835 A | 3/2000 | Hoover et al. | |
| 6,077,933 A | 6/2000 | Lee et al. | |
| 6,316,253 B1 | 11/2001 | Innis et al. | |
| 2003/0036113 A1 | 2/2003 | Reff | |
| 2003/0064395 A1* | 4/2003 | Chung | 435/6 |
| 2004/0029229 A1 | 2/2004 | Reeves et al. | |

FOREIGN PATENT DOCUMENTS

WO WO-98/41645 A1 9/1998

OTHER PUBLICATIONS

Lesk et al, Prediction of Protein Function from Protein Sequence and Structure, p. 27 and 28, downloaded Sep. 16, 2007.*
Myers, Richard M. et al., "Fine Structure Genetic Analysis of a β-Globin Promoter," *Science*, vol. 232:613-618 (1986).
Reeves, P.J. et al., "Structure and function in rhodopsin: High level expression of a synthetic bovine opsin gene and its mutants in stable mammalian cell lines," *Proc. Natl. Acad. Sci. USA*, vol. 93:11487-11492 (1996).
Velan, Baruch et al., "N-glycosylation of human acetylcholinesterase: effects on activity, stability and biosynthesis," *Biochem. J.*, vol. 296:649-656 (1993).
European Search Report for Application No. EP04783263, dated Jul. 11, 2007.
Barnett et al., Antibody Production in Chinese Hamster Ovary Cells Using an Impaired Selectable Marker. In Antibody Expression and Engineering: ACS Symposium Series, 207th National Meeting, Mar. 1994, edited by H. Wang and T. Imanaka, pp. 27-40. Washington DC: American Chemical Society, 1995.###.
Berg et al., Molecular and Cellular Biology (1983) 3:1246.
Bird et al., Science (1988) 242:423-426.
Fishwild et al., Nature Biotechnology (1996) 14:845.
Gellissen et al., Antonie Van Leeuwenhoek (1992) 62:79-93.
Goeddel, Methods Enzymol. (1990) 185:3-7.
Gritz et al., Gene (1983) 25:179-188.
Haynes et al., Nucl. Acids Res. (1983) 11:687-706.
Hieter et al., Cell (1980) 22:197.
Huston et al., Proc. Natl. Acad. Sci. U.S.A. (1988) 85:5879-5883.
Kaufman, Methods Enzymol. (1990) 185:537-566.
Kaufman et al., Proc. Natl. Acad. Sci. U.S.A. (1986) 83:3136-3140.
M. Kozak, Nucl. Acids Res. (1987) 15:8125.
Lau et al., Mol. Cell. Biol. (1984) 4:1469-1475.
Lemon & Tijan, Genes Dev. (1999) 14:15.
Littlefield et al., Science (1964) 145:709-710.
Mantovani, Gene (1999) 239:15.
Mulligan et al., Proc. Natl. Acad. Sci. U.S.A. (1981) 78:2072-2076.
Nenoi et al., Gene (1996) 175:179.
Nunberg et al., Cell (1980) 19:355.
Palmer et al., Proc. Natl. Acad. Sci. U.S.A. (1987) 84:1055-1059.
Rees et al., Biotechniques (1996) 20:102.
Reff & Parr, Gene amplification in mammalian cells: a comprehensive guide, Rodney Kellems, ed., p. 355. New York: Marcel Dekker, 1993.
Romanos et al., Yeast (1992) 8:423-488.
Stuve et al., Mol. and Cell Biology (1990) 10:972.
Takebe et al., Molecular and Cellular Biology (1988) 8:466.
Urlaub et al., Som. Cell. Molec. Genet. (1986) 12:555.
Ward et al., Nature (1989) 341:544-546.
Ward et al., J. Biol. Chem. (1990) 265:3030.
Who, J. Immunogenetics (1976) 3:357.

* cited by examiner

*Primary Examiner*—Maria Marvich
(74) *Attorney, Agent, or Firm*—Lahive & Cockfield, LLP; Jane E. Remillard, Esq.; Jeanne M. DiGiorgio, Esq.

(57) ABSTRACT

This invention provides nucleic acids and expression vectors, and host cells transformed with the same, for providing high expression of a desired polypeptide. Also provided are methods of using the expression vectors, nucleic acids, and host cells which have been modified by these compositions, for increasing expression of a gene encoding a desired polypeptide.

17 Claims, 8 Drawing Sheets

```
         AvrII          murine beta globin major promoter
   1     CCTAGGAGTA GCTTTGCTTC TCAATTTCTT ATTTGCATAA TGAGAAAAAA AGGAAAATTA

61     ATTTTAACAA CCAATTCAGT AGTTGATTGA GCAAATGCGT TGCCAAAAAG GATGCTTTAG

121     AGACAGTGTT CTCTGCACAG ATAAGGACAA ACATTATTCA GAGGGAGTAC CCAGAGCTGA

181     GACTCCTAAG CCAGTGAGTG GCACAGCATC CAGGGAGAAA TATGCTTGTC ATCACCGAAG

241     CCTGATTCCG TAGAGCCACA CCCTGGTAAG GGCCAATCTG CTCACACAGG ATAGAGAGGG

301     CAGGAGCCAG GGCAGAGCAT ATAAGGTGAG GTAGGATCAG TTGCTCCTAC ATTTGCTTCT
                                                           DHFR

361     GACATAGTTG TGTTGCGCGC TGTACAACAG CTCAGGGCTG CGATTTCGCG CCAAACTTGA

421     CGCAATCCT AGCGTGAAGG CTGGTAGGAT TTTATCCCCG CTGCCATCAT GGTTGCACCA

481     TTGAACTGCA TCGTCGCCGT GTCCCAAAAT ATGGGGATTG GCAAGAACGG AGACCTACCC

541     TGGCCTCCGC TCAGGAACGA GTTCAAGTAC TTCCAAAGAA TGACCACAAC CTCTTCAGTG
```

Figure 1A

```
601   GAAGGTAAAC AGAATCTGGT GATTATGGGT AGGAAAACCT GGTTCTCCAT TCCTGAGAAG
661   AATCGACCTT TAAAGGACAG AATTAATATA GTTCTCAGTA GAGAACTCAA AGAACCACCA
721   CGAGGAGCTC ATTTTCTTGC CAAAAGTTTG GATGATGCCT TAAGACTTAT TGAACAACCG
781   GAATTGGCAA GTAAAGTAGA CATGGTTTGG ATAGTCGGAG GCAGTTCTGT TTACCAGGAA
841   GCCATGAATC AACCAGGCCA CCTCAGACTC TTTGTGACAA GGATCATGCA GGAATTTGAA
901   AGTGACACGT TTTTCCCAGA AATTGATTTG GGGAAATATA AACTTCTCCC AGAATACCCA
961   GGCGTCCTCT CTGAGGTCCA GGAGGAAAAA GGCATCAAGT ATAAGTTTGA AGTCTACGAG
1021  AAGAAAGACT AACAGGAAGA TGCTTTCAAG TTCTCTGCTC CCCTCCTAAA GCTATGCATT
                                        SV40 pA
1081  TTTATAAGAC CATGGGACTT TTGCTGGCTT TAGAAAGGGC GAATTCAACT TGTTTATTGC
1141  AGCTTATAAT GGTTACAAAT AAAGCAATAG CATCACAAAT TTCACAAATA AAGCATTTTT
1201  TTCACTGCAT TCTAGTTGTG GTTTGTCCAA ACTCATCAAT GTATCTTATC ATGTCTGAGT
```

```
                    murine beta globin major promoter
1261    AGCTTTGCTT CTCAATTTCT TATTTGCATA ATGAGAAAAA AAGGAAAATT AATTTTAACA

1321    ACCAATTCAG TAGTTGATTG AGCAAATGCG TTGCCAAAAA GGATGCTTTA GAGACAGTGT

1381    TCTCTGCACA GATAAGGACA AACATTATTC AGAGGGAGTA CCCAGAGCTG AGACTCCTAA

1441    GCCAGTGAGT GGCACAGCAT CCAGGGAGAA ATATGCTTGT CATCACCGAA GCCTGATTCC

1501    GTAGAGCCAC ACCCTGGTAA GGGCCAATCT GCTCACACAG GATAGAGAGG GCAGGAGCCA

1561    GGGCAGAGCA TATAAGGTGA GGTAGGATCA GTTGCTCCTA CATTTGCTTC TGACATAGTT neo
1621    GTGGATGGAT CGTTTTCCAT GATT...
``` pAGE2 murine beta globin major promoter sequence:   (SEQ ID NO:2)

1    AGCTTTGCTT CTCAATTTCT TATTTGCATA ATGAGAAAAA AAGGAAAATT AATTTAACA ACCAATTCAG

71   TAGTTGATTG AGCAAATGCG TTGCCAAAAA GGATGCTTTA GAGACAGTGT TCTCTGCACA GATAAGGACA

RsaI

141  AACATTATTC AGAGGGAGTA CCCAGAGCTG AGACTCCTAA GCCAGTGAGT GGCACAGCAT CCAGGGAGAA

211  ATATGCTTGT CATCACCGAA GCCTGATTCC GTAGAGCCAC ACCCTGGTAA GGGCCAATCT GCTCACACAG

281  GATAGAGAGG GCAGGAGCCA GGGCAGAGCA TATAAGGTGA GGTAGGATCA GTTGCTCCTA CATTTGCTTC

MslI

351  TGACATAGTT GTGGATGGAT CGTT pAGE8 modified murine beta globin major promoter sequence:   (SEQ ID NO:3)

1    AGCTTTGCTT CTCAATTTCT TATTTGCATA ATGAGAAAAA AAGGAAAATT AATTTAACA ACCAATTCAG

71   TAGTTGATTG AGCAAATGCG TTGCCAAAAA GGATGCTTTA GAGACAGTGT TCTCTGCACA GATAAGGACA

Δ199

141  AACATTATTC AGAGGGAGT T TGTGGATGGA TCGTT

Figure 2A pAGE9 modified murine beta globin major promoter sequence: (SEQ ID NO:4)

```
  1  AGCTTTGCTT CTCAATTTCT TATTTGCATA ATGAGAAAAA AAGGAAAATT AATTTTAACA ACCAATTCAG
 71  TAGTTGATTG AGCAAATGCG TTGCCAAAAA GGATGCTTTA GAGACAGTGT TCTCTGCACA GATAAGGACA
                                      Δ128
141  AACATTATTC AGAGGGGAGT A GGGCAGGAGC CAGGGCAGAG CATATAAGGT GAGGTAGGAT CAGTTGCTCC
                                          MslI
211  TACATTTGCT TCTGACATAG TTGTGGATGG ATCGTT
```

Figure 2B

EXPRESSION VECTOR

CROSS REFERENCE TO RELATED APPLICATION

This application claims the benefit of U.S. Provisional Application No. 60/500,803, filed Sep. 4, 2003, which is hereby incorporated by reference in its entirety.

FIELD OF THE INVENTION

This invention relates to vectors for high expression of one or more genes of interest in host cells, such as mammalian cells, and the like.

BACKGROUND OF THE INVENTION

Stable production of a gene of interest (GOI) can be accomplished by transfecting host cells with vectors containing the GOI co-linked to a selectable marker gene, and selecting for cells harboring the GOI by inflicting a stress on the cell which can only be abated if the cell expresses sufficient quantities of the selectable marker. The vectors randomly integrate into the host cells' chromosomal DNA, and resulting transfectants show a large degree of variation in the expression level of the GOI. However, relatively few transfectant cell clones will express the GOI at the desired highest levels due to the positional effect of the site of integration. The level of expression of the genes encoded by the vector is influenced largely by the local chromosomal environment at the site of the genes' integration. (Barnett et al., 1995, *Antibody Expression and Engineering*, Wang and Imanaka (eds.), ACS Symposia Series, p. 604).

The use of a weakened selectable marker has been correlated with a shift towards obtaining transfectants with higher levels of expression of the linked GOI, presumably by biasing selection for integration positions that have positive influences on the expression of the weakened selectable marker and the co-linked GOI (Reff and Pfarr, 1992, *Gene Amplification in Mammalian Cells*, R. E. Kellems (ed.), Marcel Dekker, Inc., p.355). The expression vectors typically described in the prior art contain strong regulatory elements to drive high-level protein expression of the GOI which is co-linked to a weak selectable marker. Strategies have been utilized previously for the impairment of expression vector selectable markers, which include crippling mutations of selectable marker protein (e.g., U.S. Pat. No. 6,316,253), artificial intronic insertions in the selectable marker gene (e.g., U.S. Pat. No. 5,733,779) and impaired expression of selectable markers in polycistronic vector constructs (e.g., U.S. Pat. No. 4,713,339 and Rees et al., 1996, Biotechniques 20:102). While each of these systems for improving expression of genes of interest may have problems associated with them, it is desirable to have an improved expression system that allows for a more efficient method of generating and screening for cells that are high producers of the gene product of interest. Thus, it is desirable to create an improved expression vector and host cell expression system that can be used to efficiently generate high quantities of any recombinant protein through stable, increased expression of a gene of interest by a host cell.

The citation and/or discussion of a reference in this section and throughout the specification is provided merely to clarify the description of the present invention and is not an admission that any such reference is "prior art" to the invention described herein.

SUMMARY OF THE INVENTION

This invention provides novel expression vectors that are capable of producing high quantities of one or more desired proteins in a host cell, particularly mammalian cells. In one aspect the invention is directed to expression vectors. In one embodiment, the expression vector contains a selectable marker gene operably linked to a regulatory nucleic acid comprising a transcriptionally impaired promoter, and one or more insertion sites for inserting a co-linked gene of interest operably linked to a regulatory sequence.

In another embodiment, the expression vector contains a selectable marker gene operably linked to a regulatory nucleic acid which comprises a beta globin gene promoter which lacks a CCAAT box sequence, and one or more genes of interest operably linked to a regulatory nucleic acid. In certain embodiments, the expression vectors also have an amplifiable marker gene. In another aspect, the invention is directed to host cells that have been transfected with an expression vector of the invention. In a particular embodiment the host cell is mammalian, e.g., CHO cell.

In yet another aspect, the invention is directed to methods for producing a polypeptide encoded by a gene of interest, comprising culturing a host cell, which contains an expression vector of the invention, under suitable conditions such that the gene of interest expresses the polypeptide. In particular embodiments, the methods of the invention produce an immunoglobulin heavy chain and an immunoglobulin light chain, thereby resulting in a functional antibody.

Other features and advantages of the instant invention will be apparent from the following detailed description and examples which should not be construed as limiting.

BRIEF DESCRIPTION OF THE DRAWINGS

FIGS. 1A-1C show the sequence of a DNA fragment (SEQ ID NO:1) containing, 5' to 3', a murine beta globin major promoter, a DHFR gene, an SV40 poly A sequence, a second murine beta globin major promoter and a portion of a neo gene.

FIGS. 2A-2B shows the sequences of the pAGE2 murine beta globin major promoter (SEQ ID NO:2) and the pAGE8 and pAGE9 modified murine beta globin major promoters (SEQ ID NOS:3 and 4). The transcriptional regulatory sequences CACCC, CCAAT and TATA are underlined. The direct repeat elements are underlined with double lines.

DETAILED DESCRIPTION OF THE INVENTION

Figure 3:
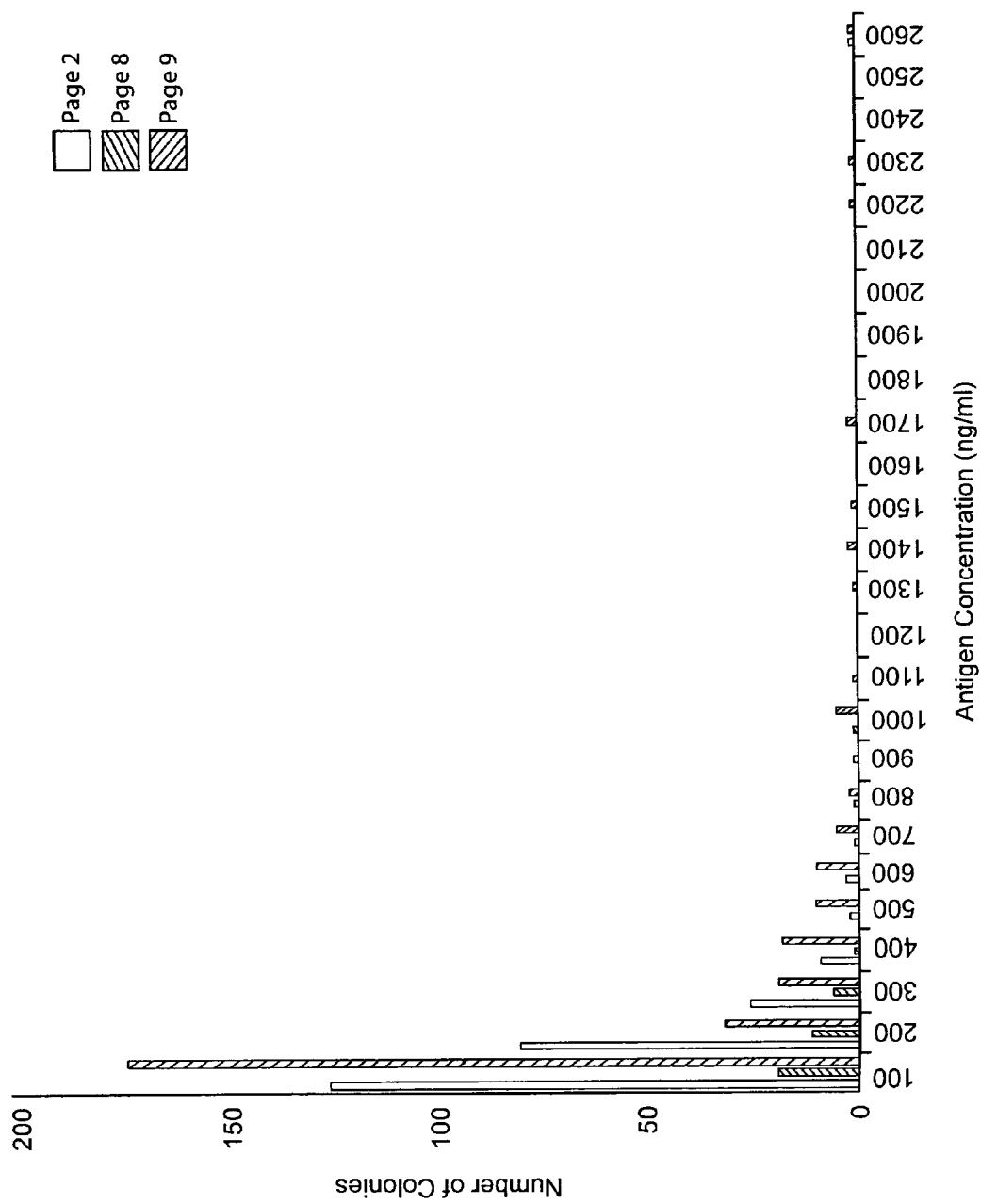
FIG. 3 is a histogram in which the number of colonies obtained by transfecting CHO cells with the pAGE2 (white bars), pAGE8 (grey bars) or pAGE9 (black bars) vectors is compared to their protein expression levels (in ng/ml).

This invention provides vectors for high levels of expression of a gene of interest (GOI). The vectors of the invention are particularly well suited for expression of recombinant antibodies (e.g., antibody heavy and light chains carried on the same expression vector) and can be used to obtain levels of antibody expression in the range of, for example 3-14 pg/cell/day. In the vectors of the invention, high level protein expression is achieved by co-linking the gene of interest (encoding the protein) to a selectable marker gene having a transcriptionally impaired promoter. In another embodiment, the selectable marker operatively linked to the transcriptionally impaired promoter is used in combination with another selectable marker that is amplifiable to achieve even greater levels of expression of the gene of interest.

Stable yet high-level expression of genes in mammalian cells is critically dependent on both the site of integration and the copy number. The selection pressure imposed by conventional concentrations of the neomycin analog G418, for example, is typically low and yields cell clones having a wide distribution of expression levels with very few clones having the higher levels of expression that typically are desirable for recombinant protein production purposes. The nucleic acids and expression vectors described herein solve this and other problems by using a selectable marker operably linked to a weakened promoter which is co-linked to a GOI. The markedly low expression of the selectable marker gene allows for a biased selection towards high-expressing clones.

This invention provides novel nucleic acid constructs (expression vectors) that are useful for stable, high-level expression of a heterologous GOI in a host cell, particularly mammalian cells. In one embodiment, the expression vectors contain (1) a selectable marker gene operably linked to a regulatory nucleic acid comprising a weakened promoter and (2) an insertion site for inserting one or more co-linked genes of interest (GOI). Insertion of a GOI operably linked to appropriate regulatory nucleic acid sequence(s) at the insertion site permits expression of the GOI in high quantity in a host cell which has been transfected with the vector. In another embodiment, the expression vectors contain (1) a selectable marker gene operably linked to a regulatory nucleic acid comprising a weakened promoter and (2) one or more GOI operably linked to a suitable regulatory nucleic acid. Thus, in this embodiment of the invention the selectable marker gene and the GOI are co-linked in the vector. Vectors of the present invention optionally contain a second selectable ("amplifiable") marker, e.g., dihydrofolate reductase (DHFR), which facilitates selection of host cells which express the GOI at high levels. Thus, an advantage of the expression vectors of the invention is that they allow increased expression of a GOI, and therefore higher production levels of the polypeptide of interest, in comparison with vectors that have the same promoter operably linked to the selectable marker gene, but which promoter has not been weakened.

Nucleic Acids

As used herein, a "nucleic acid" includes DNA, RNA, mRNA, cDNA, genomic DNA, and analogs thereof, from prokaryotes, eukaryotes and synthetic sources. A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory nucleic acids (or "control elements"). The boundaries of the coding sequence are determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or procaryotic DNA, and even synthetic DNA sequences. A transcription termination sequence is typically located 3' to the coding sequence.

Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waternan algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook et al., 1989, *Molecular Cloning: A Laboratory Manual*, Cold Spring Harbor Laboratories, New York; or Ausubel et al. (Eds.), *Current Protocols In Molecular Biology*, John Wiley & Sons, Inc., New York (1997)). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, Nucleic Acid Hybridization: A Practical Approach, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, see Sambrook, et al., supra or Ausubel et al., supra).

A first polynucleotide is "derived from" second polynucleotide if it has the same or substantially the same basepair sequence as a region of the second polynucleotide, its cDNA, complements thereof, or if it displays sequence identity as described above. A first polypeptide is "derived from" a second polypeptide if it is (i) encoded by a first polynucleotide derived from a second polynucleotide, or (ii) displays sequence identity to the second polypeptides as described above.

Selectable Markers

It is noted that in order to distinguish between selectable markers used for selecting host cells that have integrated the GOI versus selectable markers used to amplify copies of the GOI, the term "amplifiable marker" is used to describe the latter. Selectable and amplifiable markers are well-known in the art, and can be chosen for use in the invention to isolate stable transfectants based on the particular expression system desired by the skilled practitioner.

The appropriate concentrations of the agents that stress the host cell, which are metabolized by the selectable marker, will vary based on the manner they are used. The parameters for such use can be readily ascertained by one having ordinary skill in the art. Cell lines deficient in genes encoding the selectable marker are also well-known in the art.

A "selectable marker" encodes a polypeptide whose expression is necessary to permit a cell, which is transfected with a nucleic acid or vector of the present invention, to survive under a certain applied stress to the cell, e.g. a toxic agent (e.g. G418). Examples of selectable marker genes that can be used in the invention include, but are not limited to, neomycin phosphotransferase, glutamine synthetase, dihydrofolate reductase, chloramphenicol acetyltransferase, hygromycin B phosphotransferase (see Gritz et al., 1983, Gene 25:179-188 and Palmer et al., 1987, Proc. Natl. Acad. Sci. USA 84:1055-1059), xanthine-guanine phosphoribosyltransferase (see Mulligan et al., 1981, Proc. Natl. Acad. Sci. USA 78:2072-2076), histidinol dehydrogenase, tryptopham synthase β subunit, blasticidin S deaminase, zeocin, asparagine synthase, hypoxanthine-guanine phosphoribosyltransferase, thymidine kinase (see Littlefield et al., 1964, Science 145:709-710), adenine phosphoribosyltransferase, P-glycoprotein, adenosine deaminase (see Kaufinan et al., 1986, Proc. Natl. Acad. Sci. USA 83:3136-3140), omithine decarboxylase, and CAD (carbamyl-P-synthetase, aspartate transcarbamylase, dihydro-orotase). Any suitable nucleic acid encoding a selectable marker can be used in the vector compositions and methods described herein. Typically, the selectable marker genes employed in this invention can be obtained from readily available sources.

In one embodiment of the invention, the selectable marker encodes a gene which confers resistance to antibiotics, e.g., neomycin (neo) resistance gene. The neomycin resistance gene of transposon Tn5 encodes for neomycin phosphotransferase II, which confers resistance to various antibiotics, including G418 and kanamycin. The optimum amount of substrate (e.g., G418) needed for selection can be individually determined for each cell line according to known methods. See Bryan L. E., 1984, Antimicrobial Drug Resistance, L. E. Bryan (ed.), Academic, NY, pp. 241-277.

In another embodiment of the invention, an "amplifiable marker" is employed in the vectors of the present invention, in order to enhance expression of the GOI. Examples of amplifiable markers include dihydrofolate reductase, P-glycoprotein, adenosine deaminase, ornithine decarboxylase, and CAD (carbamoyl-P-synthetase, aspartate transcarbamylase, dihydroorotase). In one embodiment of an expression vector of the invention, neo is used as a selectable marker and DHFR as the amplifiable marker to allow for increased expression of GOI. DHFR is necessary for purine biosynthesis and, in the absence of exogenous purines, DHFR is required for growth of cells. Methotrexate (MTX) is a potent competitive inhibitor of DHFR, so increasing MTX concentration selects for cells that express increased levels of DHFR. Conventional DHFR amplification methods allow for the isolation of stably amplified cells that contain the amplified DHFR genes, as well as the GOI, within their chromosomes. For uses of DHFR genes and MTX as selectable markers and for gene amplification, see Maniatis et al., (1992) In: Molecular Cloning, A Laboratory Manual, Cold Spring Harbor, Cold Spring Harbor, N.Y.

Gene of Interest

A "gene of interest" (GOI) is any nucleic acid sequence for which increased transcriptional expression is desired. The GOI may encode a functional nucleic acid molecule (e.g., an RNA, such as an antisense RNA molecule) or, more typically, encodes a peptide, polypeptide or protein for which increased production is desired. The vectors of the invention can be used to express a "heterologous" GOI. As used herein, the term "heterologous" means a nucleic acid sequence or polypeptide that originates from a foreign species, or that is substantially modified from its original form if from the same species. Furthermore, an unmodified nucleic acid sequence or polypeptide that is not normally expressed in a cell is considered heterologous. Vectors of the invention can have one or more GOIs, inserted at the same or different insertion site, where each GOI is operably linked to a regulatory nucleic acid sequence which allows expression of the GOI. Thus, the vectors of the invention can be used to express various types of proteins, including, e.g., monomeric, dimeric and multimeric proteins. In other embodiments, the vectors of the invention can be used to express essentially any gene of interest, particularly genes encoding recombinant proteins having therapeutically useful activity or other commercially relevant applications. Non-limiting examples of GOIs of the invention include: erythropoietin, human growth hormone, insulin, interferons alpha, beta and/or gamma, interleukins, such as interleukin-2 and hematopoietic factors such as Factor VIII and Factor IX.

In one embodiment, the GOI encodes an antibody heavy chain or light chain, which can be of any antibody type, e.g., murine, chimeric, humanized and human, where the two chains can come from the same or different antibodies. A GOI encoding a heavy chain or light chain may encode only a fragment of the heavy chain or light chain, e.g., the antigen binding portion or Fc binding portion or a combination of both. Those of ordinary skill in the art will appreciate the term "antigen-binding portion" of an antibody refers to one or more fragments of an antibody that retain the ability to bind to an antigen. It has been shown that the antigen-binding function of an antibody can be performed by fragments of a full-length antibody. Examples of binding fragments encompassed within the term "antigen-binding portion" of an antibody include but are not limited to: (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., 1989, Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., 1988, Science 242:423-426; and Huston et al., 1988, Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

Regulatory Nucleic Acids

A regulatory nucleic acid is any sequence that regulates or affects (i) transcription, (ii) translation, or (iii) post-translational modifications, during expression of a gene operably linked the the regulatory nucleic acid, and which contains one or more "control elements" for regulating such activity. A regulatory nucleic acid and operably linked gene need not derive from the same organism or cell type. Preferably, the regulatory nucleic acid is mammalian or viral in origin.

The term "control element" of a regulatory nucleic acid is well known in the art (see, e.g., Goeddel, Gene Expression Technology, *Methods in Enzymology* 185, Academic Press, San Diego, Calif., 1990), and includes, e.g., transcriptional promoters, transcriptional enhancer elements, transcriptional termination signals, polyadenylation sequences (located 3' to the translation stop codon), sequences for optimization of initiation of translation (located 5' to the coding sequence), translation termination sequences, sequences that direct post-translational modification (e.g., glycosylation sites), all of which may be used to regulate the transcription and/or translation of a gene operably linked to a regulatory sequence. It shall be appreciated by those skilled in the art that the selection of control elements of a regulatory nucleic acid will depend on such factors as the choice of the host cell to be transformed, the level of expression of protein desired, etc.

As used herein, "operably linked" refers to an arrangement of elements, e.g., a functional linkage between a regulatory nucleic acid and a gene, wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered operably linked to the coding sequence.

The term "promoter" includes any nucleic acid sequence sufficient to direct transcription in a eukaryotic cell, including inducible promoters, repressible promoters and constitutive promoters. Typically a promoter includes elements that are sufficient to render promoter-dependent gene expression controllable in a cell type-specific, tissue-specific or temporal-specific manner, or inducible by external signals or agents. Such elements can be located in the 5' or 3' or intron sequence regions of a particular gene. Ordinarily, gene expression will be constitutive, although regulatable promoters can be employed in the present invention if desired. Examples of suitable regulatable promoters are Tet, ecdysone and lac repressor sequences. Gene expression can also be controlled by transcription-regulation using heat, light, or metals, such as by the use of metallothionine genes or heat shock genes. Those of ordinary skill in the art will appreciate that in a commercial use of the present invention, it is desirable to use non-inducible, non-regulatable promoters such as, for example, the beta globin gene, CMV, ubiquitin and SR alpha.

Promoters for use in the present invention include viral, mammalian and yeast promoters, e.g., murine beta globin promoter, ubiquitin promoter, polyoma promoter, mammalian CMV promoter, yeast alcohol oxidase, phosphoglycer-okinase promoter, lactose inducible promoters, galactosidase promoter, adeno-associated viral promoter, poxvirus promoter, retroviral promoters, rous sarcoma virus promoter, adenovirus promoters, SV40 promoter, hydroxymethylglutaryl coenzyne A promoter, thymidine kinase promoter, or H5R poxvirus promoters, adenovirus type 2MPC late promoter, alpha-antrypsin promoter, fox IX promoter, immunoglobulin promoter, CFTR surfactant promoter, albumin promoter and transferrin promoter. A promoter selected for use with nucleic acids and expression vectors of the invention can provide for (1) high levels of expression, e.g., in driving expression of the GOI, or (2) decreased levels of expression (after weakening by modification), e.g., in driving expression of the selectable marker gene. Preferably, the promoter driving the GOI is a strong promoter, e.g., ubiquitin, CMV, and SR alpha promoters, to increase expression and promote correct splicing of the product of interest. In one embodiment, the selectable marker gene is under control of the murine beta globin gene promoter and the GOI is under control of SR alpha promoter (Takebe et al., 1988, *Molecular and Cellular Biology* 8:466) or human ubiquitin C promoter (Nenoi et al., 1996, *Gene* 175:179).

In the present invention, a promoter used to drive expression of the selectable marker gene is modified such that one or more transcriptional regulatory elements are disrupted, i.e., the one or more elements' ability to drive expression of an operably linked gene is weakened in comparison to a promoter that is not modified. A "transcriptional regulatory element" is any nucleic acid sequence encoding a transcription factor binding site or enhancer element within a promoter involved in the expression of an operably linked selectable marker gene, but excludes the TATA box or similar RNA polymerase II binding site, i.e., the TATA box sequence is not modified in the present invention. Transcription factor binding sites and enhancer elements within promoters are well known in the art (see, e.g., Lemon & Tijan, 1999, Genes Dev. 14: 15; Molecular Biology of the Cell, 2002, 4th ed. B. Alberts et al. (eds), Garland Science). A regulatory nucleic acid used in the present invention, having its promoter region modified, which results in a weakened promoter, is referred to herein as a "transcriptionally impaired regulatory nucleic acid". In the present invention, a modification to the transcriptionally impaired regulatory nucleic acid is made within 300 nucleotides, preferably within 250 nucleotides, more preferably within 200 nucleotides, still more preferably within 150 nucleotides and most preferably within 100 nucleotides upstream of the TATA box, or a similar RNA polymerase II binding site sequence. Examples of transcriptional regulatory elements that can be modified in a promoter used in this invention include CCATT box sequence and CACCC element.

A transcriptional regulatory element within the promoter driving expression of an operably linked selectable marker gene can be modified using any suitable means for modifying nucleic acids available in the art to achieve the weakened state desired. For example, the modification can be one or more nucleotide insertions, deletions, substitutions, or combinations thereof, thereby causing a change to one or more transcriptional regulatory elements. If the modification selected is a deletion, e.g., a deletion of a large stretch of nucleic acid sequence (but which excludes the typical deletions to the 5' end, i.e., truncation, made to promoters for the purpose of making them manageable without compromising their transcriptional driving activity), it can be an internal deletion, which results in the desired weakened promoter. The specific modification made to the promoter in order to weaken is not important, provided a modification is made to one or more transcriptional regulatory nucleic acids which results in a weakened promoter relative to the unmodified promoter. Preferably, the modification made to the promoter is such that expression of the selectable marker is weakened to the extent that the number of viable colonies resulting after transfection of a vector of the invention is substantially diminished in comparison with an unmodified promoter driving the selectable marker gene, as demonstrated, e.g., in the Examples, infra (see Example 4).

In a particular embodiment, the promoter which drives the selectable marker gene is the well-characterized murine beta globin major promoter (Berg at al., 1983, *Mol. and Cell. Biology* 3:1246; Ward et al., 1990, *J. Biological Chemistry* 265:3030; Stuve et al., 1990, *Mol. and Cell Biology* 10:972; U.S. Pat. No. 5,733,779; and U.S. Pat. No. 6,042,835). This particular promoter requires an enhancer to be active in non-erythroid cells. In Chinese hamster ovary (CHO) cell transfectants, the strength of the murine beta globin promoter was shown to be dependent on its proximity to powerful enhancers on the same vector DNA (Reff, M. E. and Pfarr, D. S. In: *Gene Amplification in Mammalian Cells* R. E. Kellems (ed.), Marcel Dekker, Inc. 355, 1992). Transcriptional regulatory elements within the murine beta globin promoter, which are important for activation of the promoter, including, e.g., the CACCC and CCAAT box elements, have been identified and characterized (Lemon & Tijan, 1999, Genes Dev. 14: 15; Mantovani, 1999, Gene 239: 15; Molecular Biology of the Cell, 2002, 4th ed. B. Alberts et al. (eds), Garland Science). In a particular embodiment of a vector of the present invention, the murine beta globin promoter driving the selectable marker gene was mutated to remove 128 base pairs within the promoter that contained the CCAAT and CACCC regulatory elements that are bound by transcription factors to decrease the strength of the promoter and to reduce the rate of initiation of transcription of the selectable marker gene. In another particular embodiment, the expression vector is engineered to further encode the amplifiable marker murine dihydrofolate reductase (dhfr), which permits higher expression levels of the GOI by gene amplification in transfectants that respond to methotrexate (MTX) treatment.

A weakened promoter used in the present invention is transcriptionally impaired by modifying one or more transcription factor binding sites (TFBS), for example by point mutation, deletion, substitution or otherwise modifying the TFBS so that a transcription factor binds weakly, i.e., to a lesser extent in comparison with an otherwise equivalent unmodified promoter. A weakened promoter according to the invention causes decreased expression of the selected marker gene operably linked thereto. A TFBS includes any nucleic acid sequence within a promoter that permits binding of a transcription factor, but excludes a TATA box sequence. They are well known in the art, and therefore can be readily identified within a promoter used in the invention. Examples of TFBS that can be modified in a promoter used in the invention include CCAAT and CACCC (see Lemon & Tijan, supra; Mantovani, supra; and Alberts et al., supra). As used herein, a "modified CCAAT box" or a "modified CACCC element" can refer to embodiments of a promoter which lacks these transcription binding factor site nucleic acid sequences by way of partial or complete deletion or other means of disruption, e.g., insertion or substitution or nucleotides, thus resulting in the desired weakened activity of the promoter.

Typically, genes (e.g., selectable markers and GOIs) are sandwiched between the promoter and a polyadenylation site. The poly A sequence used can be from the gene of interest (i.e., the native poly A sequence can be used) or a heterologous poly A sequence can be used (i.e., from a gene different from the GOI), e.g., BGH polyA and SV40 polyA. An mRNA is transcribed from the promoters and stabilized by the polyadenylation signals located 3' to the coding regions. Poly A signals are well-known in the art, and can be selected based on suitability for use with the vectors and host cells employed in the present invention. Examples of poly A signals that can be used include human BGH poly A, SV40 poly A, human beta actin polyA, rabbit beta globin polyA, immunoglobulin kappa polyA.

Expression Vectors

The aforementioned components of expression systems of the present invention, i.e., selectable marker gene, GOI, and appropriate regulatory sequences, can be incorporated into a number of suitable backbone vectors to facilitate manipulation of the expression vectors and constructs. In addition, incorporation of the components into a vector containing means that allow replication in a microorganism greatly facilitates propagation and isolation of the constructs (i.e., creating shuttle vectors). The terms "vector" and "expression vector" are used interchangeably herein, and refer to any nucleic acid, preferably DNA, which contains (1) a selectable marker gene operably linked to a regulatory nucleic acid that contains a weakened promoter, and (2) an insertion site for introducing a GOI operably linked to a regulatory nucleic acid. Thus, in a particular embodiment of the invention, where the vector contains a selectable marker gene and GOI, the two genes are considered co-linked. As used herein, the term "co-link", and grammatical variations thereof, refers to distinct two nucleic acids, typically genes, which reside in a continuous stretch of DNA in the same vector (although there can be intervening DNA between the two co-linked DNA sequences on the vector).

Vectors used in the present invention include any nucleic acid construct capable of directing the expression of a GOI and which can transfer gene sequences to target cells, and therefore include a promoter, which is operably linked to the gene for which expression is desired. In addition to components of the vector which may be required for expression of a gene, vectors may also include a bacterial origin of replication, additional selectable marker or amplifiable genes, a signal sequence allowing the vector to exist as single-stranded DNA (e.g., M13 origin of replication), a multiple cloning site, and a mammalian origin of replication (e.g., a SV40 or adenovirus origin of replication). Vector backbones are discussed in further detail below. Vectors are capable of transferring gene sequences to target cells (e.g., viral vectors, non-viral vectors, particulate carriers, and liposomes). Vectors can be of any type including cloning, expression, and from any source inclunding viral. In one embodiment, the vector is a mammalian expression vector.

An expression vector typically includes one or more elements for means of replication, e.g., origin of replication, which can be episomal or chromosomal. Preferably, the replication sequence renders the vector capable of both means, such that the vector is capable of self-replication as an extra-chromosomal unit and of integration into the chromosome, either due to the presence of a translocatable sequence, such as an insertion sequence or transposon, due to substantial homology with a sequence present in the chromosome or due to non-homologous recombinational events. The replication sequence or replicon will be one recognized by the transformed host and is derived from any convenient source, such as from a plasmid, virus, the host cell, e.g., an autonomous replicating segment, by itself, or in conjunction with a centromere, or the like. The particular replication sequence is not critical to the subject invention and various sequences may be employed. Conveniently, a replication sequence of a virus can be employed.

Expression vectors and methods for their preparation are well known in the art (see, e.g., Maniatis et al., supra), or they can be obtained through a commercial vendor, e.g., Invitrogen (Carlsbad, Calif.), Promega (Madison, Wis.), and Statagene (La Jolla, Calif.) and modified as needed. Examples of commercially available expression vectors include pcDNA3 (Invitrogen) and pCMV-Script (Stratagene). Vector components, regulatory nucleic acids, selectable marker genes, amplifiable markers, and GOI are typically available from a commercial source or can be isolated from a natural source (e.g., animal tissue or microorganism) or prepared using a synthetic means such as PCR. The arrangement of the components can be any arrangement practically desired by one of ordinary skill in the art.

Vectors used in the present invention can be derived from viral genomes that yield virions or virus-like particles, which may or may not replicate independently as extrachromosomal elements. Virion particles containing the DNA for the high expression locus can be introduced into the host cells by infection. The viral vector may become integrated into the cellular genome. Examples of viral vectors for transformation of mammalian cells are SV40 vectors, and vectors based on papillomavirus, adenovirus, Epstein-Barr virus, vaccinia virus, and retroviruses, such as Rous sarcoma virus, or a mouse leukemia virus, such as Moloney murine leukemia virus. For mammalian cells, electroporation or viral-mediated introduction can be used.

Figure 4:
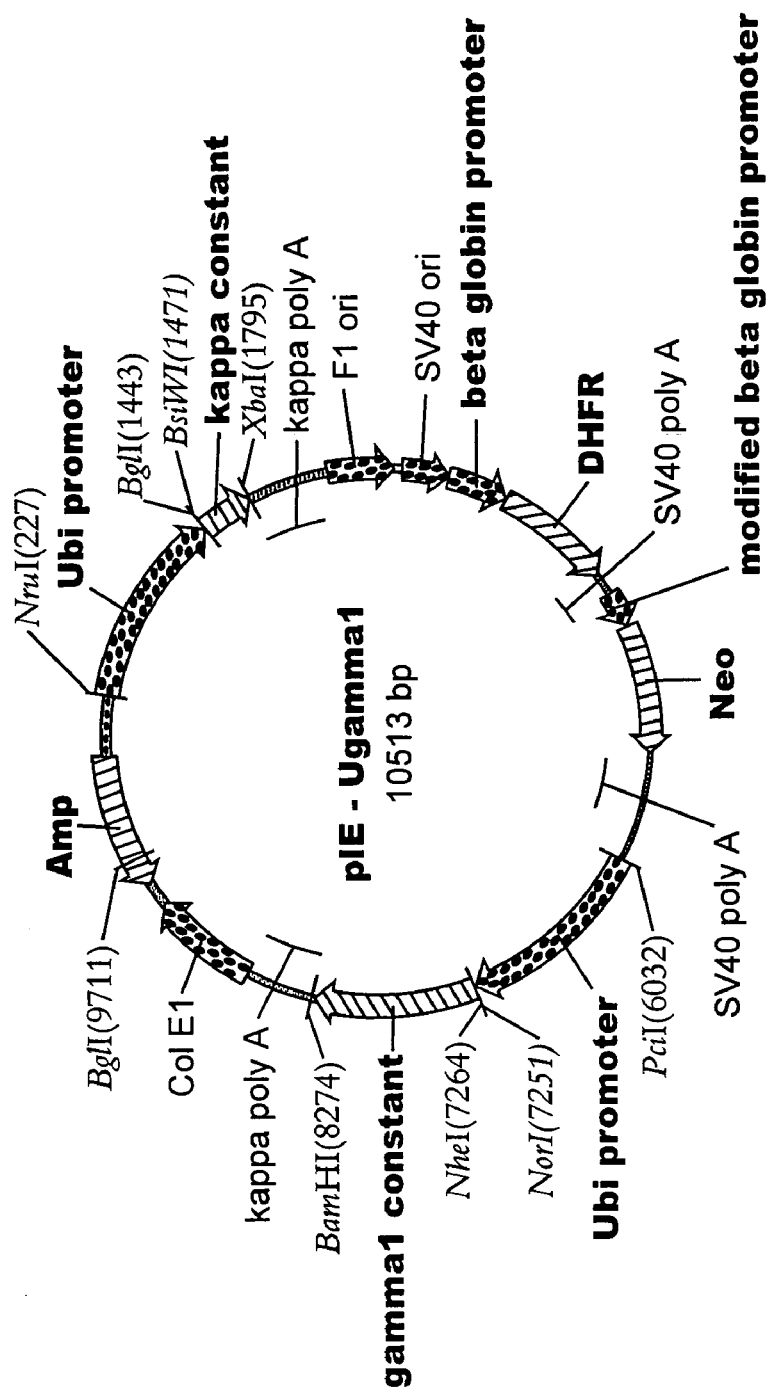
FIG. 4 is a schematic diagram of the pIE-Ugamma1 vector.

An example of an expression vector used in the present invention is described in FIG. 4. This particular embodiment can be used for expressing heavy and light chains of an antibody. A light chain variable region (i.e., a first gene of interest) can be inserted at the BglII/BsiWI restriction site. A heavy chain variable region (i.e., a second gene of interest) can be inserted at the NheI/NotI restriction site. One having ordinary skill in the art could modify the expression vector depicted in FIG. 4 to express other genes of interest by removing the kappa constant and gamma1 constant regions, which are sequences useful for generating antibody chains. Regulatory nucleic acids, e.g., kappa poly A, can also be changed to suit the needs of the practitioner.

Host Cells and Preparation

Any cell type capable of gene expression via a nucleic acid or expression vector of the present invention can be used in the present invention as a host cell. The term "host cells" refers to cells that have been transformed with a vector constructed using recombinant DNA techniques and encoding at least one heterologous gene, i.e., the selectable marker gene operably linked to a weakened promoter. In one embodiment, the host cell is sensitive to aminoglyconide antibiotics, such as G418, and capable of harboring kanamycin or neomycin resistance genes for expression therein, e.g., HeLa cells, CV-1 cells, CHO cells, 3T3 cells, L cells, or TC7 cells.

Those having ordinary skill in the art can select a particular host cell line which is best suited for expressing the GOI and selectable marker gene via a vector of the present invention. Cells that can be employed in this invention include mammalian and yeast cells (e.g., Sacchromyces cerevisiae) and cell lines and cell cultures derived therefrom. Mammalian cells, e.g., germ cells or somatic cells, can be derived from mammals, such as mice, rats, or other rodents, or from primates, such as humans or monkeys. It shall be understood that primary cell cultures or immortalized cells can be employed in carrying out the techniques of this invention.

In particular embodiments, the cell type is mammalian or yeast in origin including, but not limited to Chinese hamster ovary (CHO) (e.g., DG44 and DUXB11; Urlaub et al., Som. Cell Molec. Genet. 12:555, 1986; Haynes et al., Nuc. Acid. Res. 11:687-706, 1983; Lau et al., Mol. Cell. Biol. 4:1469-1475, 1984; Methods in Enzymology, 1991, vol. 185, pp537-566. Academic Press, Inc., San Diego, Calif.), Chinese hamster fibroblast (e.g., R1610), human cervical carcinoma (e.g., HELA), monkey kidney line (e.g., CVI and COS), murine fibroblast (e.g., BALBc/3T3), murine myeloma (P3×63-Ag3.653; NS0; SP2/O), hamster kidney line (e.g., HAK), murine L cell (e.g., L-929), human lymphocyte (e.g., RAJI), human kidney (e.g., 293 and 293T), yeast host cell systems (e.g., as described in RE 35749; U.S. Pat. No. 5,629,203; Gellissen et al., Antonie Van Leeuwenhoek 62:79-93 (1992); Romanos et al., Yeast 8:423-488 (1992); Goeddel, Methods in Enzymology 185 (1990); Guthrie and Fink, Methods in Enzymology 194 (1991). Host cell lines are typically commercially available (e.g., from BD Biosciences, Lexington, Ky.; Promega, Madison, Wis.; Life Technologies, Gaithersburg, Md.) or from the American Type Culture Collection (ATCC, Manassas, Va.).

Nucleic acids and expression vectors can be introduced or transformed into an appropriate host cell by various techniques well known in the art (see, e.g., Ridgway, 1973, Vectors: Mammalian Expression Vectors, Chapter 24.2, pp. 470-472, Rodriguez and Denhardt eds., Butterworths, Boston, Mass.; Graham et al., 1973, Virology 52:456; Sambrook et al., 1989, Molecular Cloning: A Laboratory Manual, Cold Spring Harbor Laboratories, New York; Davis et al., 1986, Basic Methods in Molecular Biology, Elsevier; and Chu et al., 1981, Gene 13:197). The terms "transformation" and "transfection", and their grammatical variations, are used interchangeably herein and refer to the uptake of foreign DNA by a cell by any means practicable. A cell has been "transformed" when an exogenous nucleic acid has been introduced inside the cell membrane. The uptake of the nucleic acid results in a stable transfectant, regardless of the means by which the uptake is accomplished, which may include transfection (including electroporation), protoplast fusion, calcium phosphate precipitation, cell fusion with enveloped DNA, microinjection, and infection with intact virus. Even transient expression at higher than normal levels is useful for functional studies or for the production and recovery of proteins of interest. Transformed cells are grown under conditions appropriate for the production of the GOI (e.g., antibody heavy and/or light chains in one embodiment), and assays are performed to identify the encoded polypeptide of interest. Exemplary assay techniques for identifying and quantifying gene products include enzyme-linked immunosorbent assay (ELISA), radioimmunoassay (RIA), or fluorescence-activated cell sorter analysis (FACS), immunohistochemistry, and the like.

In the present invention, it is preferred that permanent (i.e., stable) transformation of a nucleic acid or vector or the invention occurs. This is accompanied by integration of the transforming DNA into the cellular genome by recombination. Insertional transformation, which results in the high expression locus being tagged, usually takes place by non-homologous recombination of the DNA construct containing the tag into a random genomic position, although it will be understood that homologous recombination can occur.

The transformed cells obtained by the method of this invention can be employed for the preparation of continuous cell lines in which the cells are essentially immortal, or for the preparation of established cell lines that have the potential to be subcultured in vitro. Continuous cell lines and established cell lines can be obtained from a variety of organisms and organs, such as rodent embryos; primate kidneys; rodent and human tumors; and fibroblast, epithelial, or lymphoid cells. Cells exhibiting the highest levels of expression can be cloned, if desired.

Cells used in the present invention can be cultured according to standard cell culture techniques, e.g., they can be fixed to a solid surface or grown in suspension in appropriate nutrient media.

The term "recombinant", as used herein to describe a nucleic acid molecule, means a polynucleotide of genomic, cDNA, semisynthetic, or synthetic origin, which by virtue of its origin or manipulation (1) is not associated with all or a portion of the polynucleotide with which it is associated in nature, and/or (2) is linked to a polynucleotide other than that to which it is linked in nature. The term "recombinant", as used herein to describe a protein or polypeptide means a polypeptide produced by expression of a recombinant polynucleotide. The term "recombinant", as used herein in reference to cells, means cells that can be or have been used as recipients for recombinant vectors or other transfer DNA, and include progeny of the original cell which has been transfected. It shall be understood that progeny of a single parental cell may not be completely identical in morphology or in genomic or total DNA complement to the original parent, due to accidental or deliberate mutation. Progeny of a parental cell which are sufficiently similar to the parent to be characterized by a relevant property, such as the presence of a nucleotide sequence encoding a desired polypeptide, are also considered progeny.

While this invention has been described with reference to expression of a desired functional polypeptide, it will be understood that a polypeptide need not necessarily be the product of interest produced by an expression vector. Hence, for example, expression vectors of the invention are useful for the production of eucaryotic gene transcription and expression products in general, including RNA.

EXAMPLES

Example 1

Construction of pAGE2 (plasmid for AntiGen Expression 2)

A pAGE2 vector was constructed from a pcDNA3.1 (+) vector backbone (Invitrogen #V790-20) by replacing the SV40 promoter that drives expression of the neomycin phosphotransferase (neo) selectable marker with the murine beta globin major promoter (Berg et al., 1983, Molecular and Cellular Biology 3:1246 and Ward et al., 1990, J. Biol. Chem. 265:3030). In addition, an expression cassette containing a murine dihydrofolate reductase (DHFR) amplifiable marker (Nunberg et al., 1980, Cell 19: 355) was inserted upstream of the neo cassette.

The region inserted into the vector backbone to create pAGE2 was a DNA derived from assembled polymerase chain reaction (PCR) amplified products consisting of a 5'→3' murine beta globin promoter, a murine DHFR coding region, a SV40 polyadenylation region (polyA) and a second murine beta globin promoter. The templates for the PCR amplification of the beta globin promoters, the DHFR coding region and the SV40 polyA were derived from Medarex HuMab Mouse® genomic DNA (see FIGS. 2A-2B; Fishwild et al., 1996, Nature Biotechnology 14:845), P3X63Ag8.653 cell line (ATCC #CRL-1580) cDNA and the vector backbone vector DNA, respectively. Alternatively, this region could have been generated by other standard molecular biology techniques, including assembly of synthetic DNA. The vector backbone was digested at unique Avr II and Bsa BI restriction enzyme sites and the 69 base pair (bp) region between these sites was replaced by the assembled DNA insert. Additionally, the nucleotides at positions –2 and –3 relative to the ATG start codon of the neo Kozak sequence were modified from CG to TC. An analysis of 699 vertebrate mRNAs showed that the TC sequence is less prevalent than the CG sequence at positions –2 and –3 (M. Kozak, 1987, Nuc. Acids Res. 15:8 125), but both of these Kozak motifs contain pyrimidines at the –3 position and are weak translation initiators.

Thus, following insertion of the assembled PCR products, the resulting pAGE2 vector contained the following elements: an ampicillin resistance gene, a viral promoter upstream of a multiple cloning site followed by a poly A sequence (to allow for insertion of a gene of interest to be expressed), an f1 ori, a murine beta globin major promoter operatively linked to the DHFR gene followed by an operatively linked SV40polyA sequence, and a second murine beta globin major promoter operatively linked to a neomycin gene followed by an operatively linked SV40poly A sequence. The annotated sequence of the inserted region is shown in FIGS. 1A-1C (SEQ ID NO: 1).

Thus, following insertion of the assembled PCR products, the resulting pAGE2 vector contained the following elements: an ampicillin resistance gene, a viral promoter upstream of a multiple cloning site followed by a poly A sequence (to allow for insertion of a gene of interest to be expressed), an f1 ori, a murine beta globin major promoter operatively linked to the DHFR gene followed by an operatively linked SV40 poly A sequence, and a second murine beta globin major promoter operatively linked to a neomycin gene followed by an operatively linked SV40 poly A sequence. The annotated sequence of the inserted region is shown in FIGS. 1A-1B (SEQ ID NO: 1).

Example 2

Construction of pAGE8 and pAGE9

In order to weaken the murine beta globin promoter driving expression of the neo selectable marker gene, transcriptional regulatory elements within the promoter were removed. The pAGE8 vector was constructed from the pAGE2 vector by removing 199 bp from the beta globin promoter between the Rsa I and Msl I restriction enzyme sites (see FIGS. 2A-2B). The pAGE9 vector was constructed from pAGE2 by removing 128 bp immediately downstream from the Rsa I restriction enzyme cleavage site in the beta globin promoter. The sequences of the pAGE2 murine beta globin major promoter (SEQ ID NO:2) and the pAGE8 and pAGE9 modified murine beta globin major promoters (SEQ ID NOS:3 and 4) are shown in FIGS. 2A-2B. The beta globin promoter of the pAGE8 vector lacks both the CCAAT and TATA elements, and the beta globin promoter of the pAGE9 vector lacks the CCAAT but retains the TATA element.

Example 3

Subcloning of a Gene of Interest into pAGE2, pAGE8 and pAGE9 Expression Vectors

A DNA sequence encoding a gene of interest (GOI), encoding a 165 amino acid secreted protein, was PCR amplified and subcloned into pAGE2, pAGE8 and pAGE9 at the Hind III and Xho I sites in each vector's multiple cloning site. The pAGE2, pAGE8 and pAGE9 GOI constructs have identical sequences except for the modifications made to the beta globin promoters driving neo expression.

Example 4

Transfection of Host Cells with pAGE2, pAGE8 and pAGE9 GOI Test Vector Constructs The Chinese hamster ovary cell line CHO DG44 (Urlaub et al., Som. Cell Molec. Genet. 12:555, 1986), which is deficient in DHFR activity, was used as host cells for expressing the GOI from the pAGE constructs. The CHO DG44 cells were adapted to growth in suspension culture in growth medium (CHO SSFMII; Invitrogen #31033-020) supplemented with HAT (100 µM hypoxanthine, 16 µM thymidine; Invitrogen #11067-030).

The pAGE2, pAGE8 and pAGE9 constructs containing GOI were linearized by digestion with Bgl II restriction enzyme. The DNAs were ethanol precipitated and resuspended in 10 mM Tris 7.6, 1 mM EDTA.

The CHO cells were prepared for transfection by washing the cells in a sucrose-buffered solution (SBS) and resuspending the cells at $1 \times 10^7$ cells/ml SBS solution. Cells (400 µl) were mixed with the pAGE construct DNAs and electroporated (four electroporations using 0.5 µg DNA and 3 electroportations using 2 µg DNA per electroporation for each construct) at 230 volts, 400 microfaradays capacitance and 13 ohms resistance (BTX Molecular Delivery Systems #600 electro cell manipulator; San Diego, Calif.). The cells were removed from the electroporation curvettes, 20 ml growth medium added, and plated into a 96 well dish using 200 µl cells per well (approximately $4 \times 10^4$ cells/well). Two days after the electroporation, 150 µl of medium was removed from each well and replaced with 150 µl selection medium [growth medium with 400 µg/ml G418 (Invitrogen #10131-035)]. Every three to seven days, 150 µl of selection medium per well was replaced with fresh selection medium. The number of wells per plate that had viable colonies of cells was counted for 34 days after the electroportation.

As shown in Table I, the seven electroporations of the pAGE2 GOI construct resulted in 118 viable colonies and the pAGE8 and pAGE9 GOI construct electroporations resulted in 0 and 1 viable colony, respectively. These data indicate that fewer cells survived G418 selection from electroporations using the pAGE8 and pAGE9 constructs that contain promoters modified to weaken expression of the neo selectable marker, as compared with electroporations using the pAGE2 construct, which had an unmodified promoter driving neo expression.

TABLE I

| Vector | Plate # | DNA (µg) | # colonies/ plate | total # colonies per vector |
|---|---|---|---|---|
| pAGE2 | 1 | 0.5 | 1 | 118 |
|  | 2 | 0.5 | 16 |  |
|  | 3 | 0.5 | 3 |  |
|  | 4 | 0.5 | 5 |  |
|  | 5 | 2 | 30 |  |
|  | 6 | 2 | 29 |  |
|  | 7 | 2 | 34 |  |
| pAGE8 | 8 | 0.5 | 0 | 0 |
|  | 9 | 0.5 | 0 |  |
|  | 10 | 0.5 | 0 |  |
|  | 11 | 0.5 | 0 |  |
|  | 12 | 2 | 0 |  |
|  | 13 | 2 | 0 |  |
|  | 14 | 2 | 0 |  |
| pAGE9 | 15 | 0.5 | 0 | 1 |
|  | 16 | 0.5 | 0 |  |
|  | 17 | 0.5 | 0 |  |
|  | 18 | 0.5 | 0 |  |
|  | 19 | 2 | 1 |  |
|  | 20 | 2 | 0 |  |
|  | 21 | 2 | 0 |  |

To obtain viable colonies from pAGE8 and pAGE9 GOI electroporations, the DNA concentration per electroporation was increased (to the amounts shown below in Table II) and CHO cells were electroporated as described above GOI. The electroporations yielded 251, 38 and 287 viable colonies for the pAGE2, pAGE8 and pAGE 9 constructs, respectively (see Table II).

TABLE II

| Vector | Plate # | DNA (µg) | # colonies/ plate | total # colonies per vector |
|---|---|---|---|---|
| pAGE2 | 1 | 1 | 88 | 251 |
|  | 2 | 1 | 48 |  |
|  | 3 | 1 | 37 |  |
|  | 4 | 2 | 42 |  |
|  | 5 | 2 | 22 |  |
|  | 6 | 2 | 14 |  |
| pAGE8 | 7 | 60 | 12 | 38 |
|  | 8 | 60 | 11 |  |
|  | 9 | 80 | 7 |  |
|  | 10 | 80 | 0 |  |
|  | 11 | 80 | 8 |  |
| pAGE9 | 12 | 40 | 26 | 287 |
|  | 13 | 40 | 34 |  |

TABLE II-continued

| Vector | Plate # | DNA (μg) | # colonies/ plate | total # colonies per vector |
|---|---|---|---|---|
| | 14 | 40 | 51 | |
| | 15 | 60 | 22 | |
| | 16 | 60 | 21 | |
| | 17 | 60 | 26 | |
| | 18 | 80 | 32 | |
| | 19 | 80 | 46 | |
| | 20 | 80 | 29 | |

When the viable colonies were approximately twenty to forty percent confluent in the wells, the concentrations in the culture supernatants of the protein encoded by the GOI were measured by ELISA on days 22, 27, 32, 36, 41 and 47 after electroporation. FIG. 3 shows a histogram comparing the number of colonies obtained for each construct with their protein expression levels. Cells electroporated with pAGE8 yielded only 38 viable colonies having low protein expression levels. Cells electroporated with the pAGE2 construct yielded 245/251 (98%) colonies with GOI expression levels under 500 ng/ml and only 1/251 (0.3%) colony with GOI expression levels over 1000 ng/ml. In contrast, the cells electroporated with the pAGE9 construct yielded 254/287 (88%) colonies with under 500 ng/ml and 10/287 (3%) colonies with over 1000 ng/ml expression levels. Thus, the pAGE9 construct, which contains modifications to the murine beta globin promoter, which drives the expression of the neo selectable marker, achieved the highest percentage of transfectant colonies producing at the highest levels of GOI protein expression.

Example 5

Construction of pIE (Plasmid for Immunoglobulin Expression)

A second vector series (termed pIE) was constructed for expression of recombinant antibodies utilizing the pAGE9 vector, which contained the modified beta globin promoter, in order to increase the number of transfectant clones that produce high levels of antibody. This vector consists of the pAGE9 vector backbone modified to contain two separate expression cassettes for the antibody light and heavy chain proteins. A representative pIE vector is shown in FIG. 4. It shall be appreciated by those of ordinary skill in the art, that the pIE vector can be modified to express any two genes of interest, e.g., subunits of a receptor complex or other protein.

The light chain expression cassette was created by modifying the protein expression cassette of the pAGE vector. The original polyA region in the protein expression cassette between the Bbs I and Xba I sites was replaced with a human kappa polyA region (Hieter et al., Cell 22:197, 1980). The Bgl II recognition site upstream of the protein expression cassette promoter was destroyed by digestion of the plasmid with Bgl II followed by Klenow treatment. A human kappa constant region was PCR amplified from a synthetic kappa constant region template utilizing primers that added a 3' Xba I site after the translational stop codon and 5' Avr II, Bgl II, Pme I, Hind III, Kpn I sites and a BsiW I site that encodes the first two codons of the kappa constant region. This PCR fragment containing the kappa constant region and restriction enzyme cloning sites was digested with Avr II and Xba I and subcloned into the Nhe I and Xba I sites in the pAGE vector protein expression cassette multiple cloning site. A strong promoter such as the human ubiquitin C promoter (U) (Nenoi et al., Gene 175:179, 1996) or the SRα promoter with the SV40 late region splice junction (SR) (Takebe et al., Molecular and Cellular Biology 8:466, 1988) was inserted between the Nru I and Bgl II sites to drive expression of the light chain. For expression of recombinant light chains, antibody kappa variable region cDNAs, including signal sequences and optimal Kozak sequences, were subcloned in frame with the kappa constant region into the Bgl II and BsiW I recognition sites.

A heavy chain expression cassette was created at the unique Pci I site downstream of the neo expression cassette. The human kappa polyA template was PCR amplified utilizing primers that added 5' Pci I, Not I, Xho I, Nhe I and BamH I sites and a 3' Nco I site. The PCR amplified product was digested with Pci I and Nco I restriction enzymes and cloned into the Pci I site of the pAGE9 vector. A human gamma1 cDNA, containing a 5' Nhe I recognition site which encodes the first two codons of the gamma1 constant region and a 3' BamH I site following the translational stop codon, was subcloned into the Nhe I and BamH I sites of the vector. A human ubiqutin C or SRα promoter was cloned into the Pci I and Not I sites of the vector. For expression of recombinant heavy chains, antibody heavy chain variable region cDNAs including signal sequences and optimal Kozak sequences typically were subcloned into the Not I and Nhe I recognition sites and in frame with the gamma constant region. See for example FIG. 4.

A series of pIE vectors were constructed in which the promoters in the heavy and light chain cassettes varied (either ubiquitin, abbreviated as U, or SRalpha, abbreviated as SR) and the gamma1 heavy chain constant region was replaced with a gamma4 constant region or with various gamma1 allotypes, including z, f and fa (WHO, J. Immunogenetics 3:357, 1976). Thus, the pIE vector series included the following vectors: pIE-Uγ1z, pIE-Uγ1f, pIE-Uγ1fa, pIE-Uγ4, pIE-SRγ1z, pIE-SRγ1f, pIE-SRγ1fa and pIE-SRγ4. The vector nomenclature represents the pIE vector backbone, the promoter driving heavy and light chain expression and the isotype and allotype of the heavy chain constant region.

Example 6

Expression of Recombinant Antibodies by CHO Cell Transfectants

Figure 5:
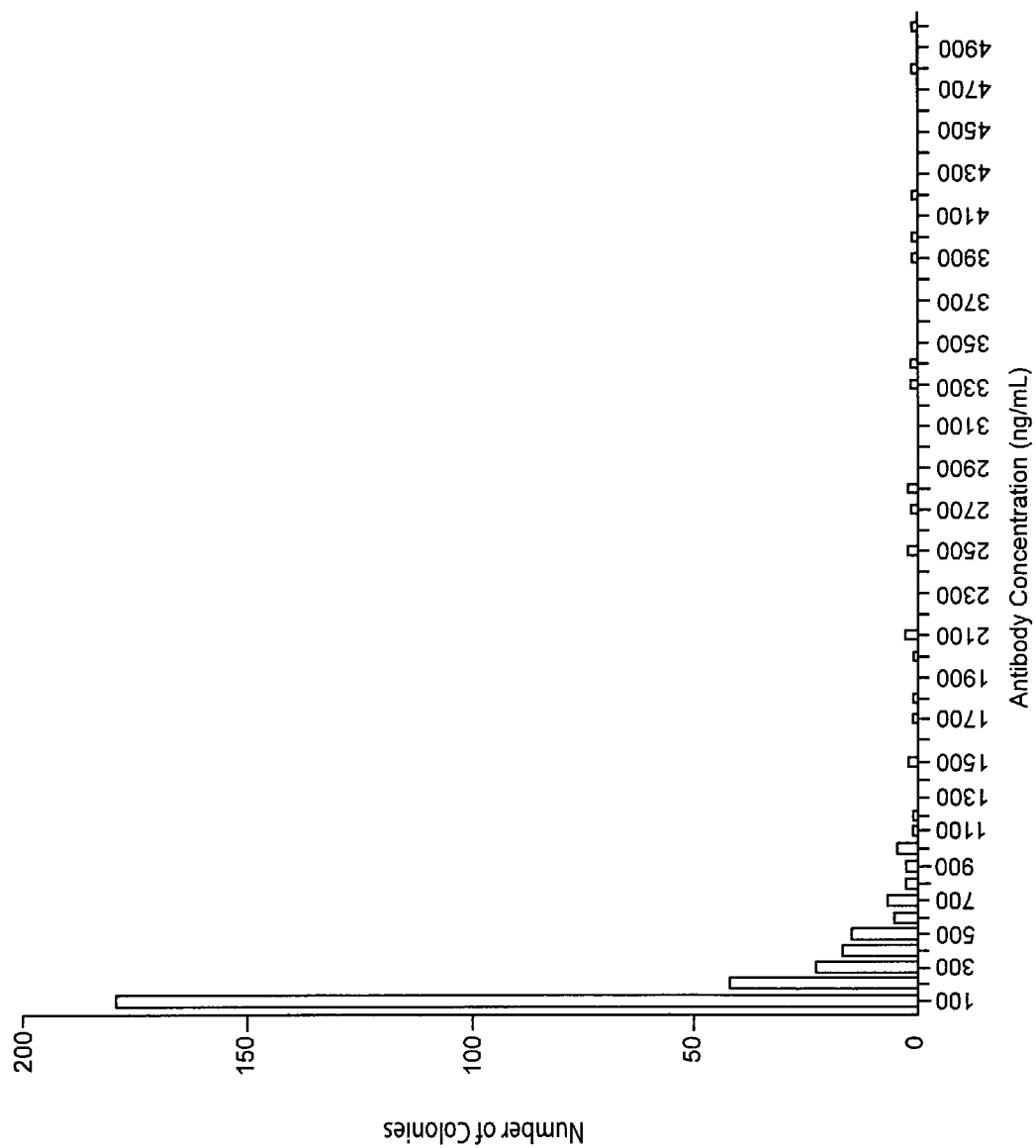
FIG. 5 is a histogram in which the number of colonies obtained by transfecting CHO cells with a pIE vector having the same beta globin promoter modification found in pAGE9 is compared with antibody expression levels (in ng/ml).

Antibody heavy and light chain variable region cDNAs derived from hybridomas producing fully human monoclonal antibodies were subcloned into the heavy and light chain expression cassettes of the pIE vectors as described above. The pIE antibody constructs were used to transfect CHO DG44 host cells using the protocol described above for the pAGE9 test GOI construct. GOI Transfection with the pIE constructs resulted in a substantial percentage of the colonies producing antibody at high levels, which was similar to the results achieved using the pAGE9 test antigen. FIG. 5 shows a histogram comparing the number of 96 well colonies expressing varying levels of representative monoclonal antibody mAb1, as measured by ELISA. At the 96 well stage, 20/322 (6%) of the colonies produced over 1000 ng/ml antibody.

Six pIE antibody contructs were used to transfect CHO cells. Less than a thousand 96 well colonies per construct were screened for IgG production levels, and for each construct, colonies producing the highest amounts of antibodies were expanded into spinner flasks and their specific productivity measured. The number of construct integration sites was determined by Southern blot analyses. Although the transfectant clones had low numbers of integration sites, they produced levels of IgG up to 14 pg/cell/day. Thus, the high level of antibody expression from each of the six pIE construct transfectants was not associated with a high number of copies of the construct integrated into many insertion sites in the host chromosomes (Table III).

TABLE III

| Human antibody | Vector | # colonies screened | Productivity (pg/cell/day) | # insertion sites |
|---|---|---|---|---|
| mAb 1 | pIE-Uγ1fa | 322 | 3 | 1 |
| mAb 1 | pIE-Uγ1fa | 322 | 8 | 5 |
| mAb 2 | pIE-SRγ1fa | 952 | 6 | 2 |
| mAb 3 | pIE-SRγ1f | 61 | 8 | 2 |
| mAb 4 | pIE-SRγ1z | 643 | 14 | 1 |
| mAb 5 | pIE-Uγ1f | 154 | 4 | 1 |
| mAb 6 | pIE-Uγ1f | 373 | 8 | ND |

Example 7

Amplification with Methotrexate (MTX) Treatment

DHFR expression cassettes were engineered into the pAGE and pIE vectors described above, and the vectors were used to transfect CHO DG44 cells. The cells were grown in CHO SSFMII Medium (Invitrogen #31033-020) supplemented with 5, 50 or 500 nM MTX in order to induce amplification. A particular transfectant making mAb4 had one integration site containing the pIE construct and produced 8 pg/cell/day prior to amplification in 50 nM MTX; following amplification, production was increased threefold accompanied by a sevenfold increase in construct copy number. In a particular transfectant making mAb1, which had one integration site and produced 3 pg/cell/day mAb, the sequential amplification in 5, 50 and 500 nM MTX increased the gene copy number eightfold and productivity twelve-fold.

Equivalents

Those skilled in the art will recognize, or be able to ascertain using no more than routine experimentation, many equivalents of the specific embodiments of the invention described herein. Such equivalents are intended to be encompassed by the following claims.

Incorporation by Reference

All patents, pending patent applications, and other publications cited herein are hereby incorporated by reference in their entireties.

What is claimed is:

1. An expression vector, comprising (i) a selectable marker gene operably linked to a regulatory nucleic acid which comprises a beta globin gene promoter; and (ii) one or more genes of interest operably linked to a second regulatory nucleic acid, wherein the beta globin gene promoter as set forth in SEQ ID NO:4 lacks a CCAAT box sequence and contains a TATA box sequence.

2. The expression vector of claim 1, wherein the selectable marker gene is a neomycin phosphotransferase gene.

3. The expression vector of claim 1, wherein the selectable marker gene is selected from the group consisting of a glutamine synthetase, a dihydrofolate reductase, a chloramphenicol acetyltransferase, a hygromycin B phosphotransferase, a xanthine-guanine phosphoribosyltransferase, a histidinol dehydrogenase, a tryptopham synthase fβ subunit, a blasticidin S deaminase, a zeocin, an asparagine synthase, a hypoxanthine-guanine phosphoribosyltransferase, a thymidine kinase, an adenine phosphoribosyltransferase, a P-glycoprotein, an adenosine deaminase, an ornithine decarboxylase, and a CAD (carbamoyl-P-synthetase, aspartate transcarbamylase, dihydroorotase) gene.

4. The expression vector of claim 1, further comprising a nucleic acid sequence comprising an amplifiable gene.

5. The expression vector of claim 4, wherein the amplifiable gene is selected from the group consisting of a P-glycoprotein, an adenosine deaminase, an ornithine decarboxylase, a dihydrofolate reductase, and a CAD (carbamoyl-P-synthetase, aspartate transcarbamylase, dihydroorotase) gene.

6. The expression vector of claim 1, further comprising a dihydrofolate reductase gene.

7. The expression vector of claim 1, wherein the at least one gene of interest comprises a gene encoding an immunoglobulin heavy or an immunoglobulin light chain.

8. A host cell transfected with the expression vector of claim 1.

9. The host cell of claim 8 which is a mammalian cell.

10. The host cell of claim 8 which is a Chinese hamster ovary cell.

11. A method for producing the at least one gene of interest, comprising culturing the cell of claim 8 under suitable conditions such that the at least one gene of interest is expressed.

12. The method of claim 11 wherein the selectable marker gene is neomycin phosphotransferase.

13. The method of claim 11 wherein culturing the cell further comprises contacting the cell with a compound such that cells expressing the selectable marker can be selected.

14. The method of claim 11 wherein the expression vector further comprises an amplifiable marker gene and wherein culturing the cell further comprises contacting the cell with a compound such that cells expressing the selectable marker can be selected.

15. The method of claim 14 wherein the amplifiable marker gene is dihydrofolate reductase.

16. The method of claim 11, wherein the at least one gene of interest is at least two genes of interest.

17. The method of claim 11 wherein the at least one gene of interest is recovered.

* * * * *

UNITED STATES PATENT AND TRADEMARK OFFICE
CERTIFICATE OF CORRECTION

PATENT NO. : 7,674,618 B2 Page 1 of 1
APPLICATION NO. : 10/934304
DATED : March 9, 2010
INVENTOR(S) : Black et al.

It is certified that error appears in the above-identified patent and that said Letters Patent is hereby corrected as shown below:

In Column 23, Claim 3, Line 29:
Delete "tryptopham" and insert -- tryptophan --

In Column 23, Claim 3, Line 29:
Delete "fβ" and insert -- β --

Signed and Sealed this

Seventh Day of December, 2010

David J. Kappos
*Director of the United States Patent and Trademark Office*

SEQUENCE LISTING

<160> NUMBER OF SEQ ID NOS: 4

<210> SEQ ID NO 1
<211> LENGTH: 1644
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
cctaggagta gctttgcttc tcaatttctt atttgcataa tgagaaaaaa aggaaaatta      60
attttaacaa ccaattcagt agttgattga gcaaatgcgt tgccaaaaag gatgctttag     120
agacagtgtt ctctgcacag ataaggacaa acattattca gagggagtac ccagagctga     180
gactcctaag ccagtgagtg gcacagcatc cagggagaaa tatgcttgtc atcaccgaag     240
cctgattccg tagagccaca ccctggtaag ggccaatctg ctcacacagg atagagaggg     300
caggagccag ggcagagcat ataaggtgag gtaggatcag ttgctcctac atttgcttct     360
gacatagttg tgttgcgcgc tgtacaacag ctcagggctg cgatttcgcg ccaaacttga     420
cggcaatcct agcgtgaagg ctggtaggat tttatccccg ctgccatcat ggttcgacca     480
ttgaactgca tcgtcgccgt gtcccaaaat atggggattg gcaagaacgg agacctaccc     540
tggcctccgc tcaggaacga gttcaagtac ttccaaagaa tgaccacaac ctcttcagtg     600
gaaggtaaac agaatctggt gattatgggt aggaaaacct ggttctccat tcctgagaag     660
aatcgacctt taaggacag  aattaatata gttctcagta gagaactcaa agaaccacca     720
cgaggagctc attttcttgc caaaagtttg gatgatgcct taagacttat tgaacaaccg     780
gaattggcaa gtaaagtaga catggtttgg atagtcggag gcagttctgt ttaccaggaa     840
gccatgaatc aaccaggcca cctcagactc tttgtgacaa ggatcatgca ggaatttgaa     900
agtgacacgt ttttcccaga aattgatttg gggaaatata aacttctccc agaataccca     960
```

```
ggcgtcctct ctgaggtcca ggaggaaaaa ggcatcaagt ataagtttga agtctacgag    1020
aagaaagact aacaggaaga tgctttcaag ttctctgctc ccctcctaaa gctatgcatt    1080
tttataagac catgggactt ttgctggctt tagaaagggc gaattcaact tgtttattgc    1140
agcttataat ggttacaaat aaagcaatag catcacaaat ttcacaaata aagcattttt    1200
ttcactgcat tctagttgtg gtttgtccaa actcatcaat gtatcttatc atgtctgagt    1260
agctttgctt ctcaatttct tatttgcata atgagaaaaa aaggaaaatt aattttaaca    1320
accaattcag tagttgattg agcaaatgcg ttgccaaaaa ggatgcttta gagacagtgt    1380
tctctgcaca gataaggaca aacattattc agagggagta cccagagctg agactcctaa    1440
gccagtgagt ggcacagcat ccagggagaa atatgcttgt catcaccgaa gcctgattcc    1500
gtagagccac accctggtaa gggccaatct gctcacacag gatagagagg gcaggagcca    1560
gggcagagca tataaggtga ggtaggatca gttgctccta catttgcttc tgacatagtt    1620
gtggatggat cgttttccat gatt                                          1644

<210> SEQ ID NO 2
<211> LENGTH: 374
<212> TYPE: DNA
<213> ORGANISM: Artificial Sequence
<220> FEATURE:
<223> OTHER INFORMATION: Description of Artificial Sequence: Synthetic
      pAGE2 murine beta globin major promoter sequence

<400> SEQUENCE: 2
agctttgctt ctcaatttct tatttgcata atgagaaaaa aaggaaaatt aattttaaca    60
accaattcag tagttgattg agcaaatgcg ttgccaaaaa ggatgcttta gagacagtgt    120
tctctgcaca gataaggaca aacattattc agagggagta cccagagctg agactcctaa    180
gccagtgagt ggcacagcat ccagggagaa atatgcttgt catcaccgaa gcctgattcc    240
gtagagccac accctggtaa gggccaatct gctcacacag gatagagagg gcaggagcca    300
gggcagagca tataaggtga ggtaggatca ggtgctccta catttgcttc tgacatagtt    360
gtggatggat cgtt                                                     374

<210> SEQ ID NO 3
<211> LENGTH: 175
<212> TYPE: DNA
<213> ORGANISM: Artificial Sequence
<220> FEATURE:
<223> OTHER INFORMATION: Description of Artificial Sequence: Synthetic
      pAGE8 modified murine beta globin major promoter sequence

<400> SEQUENCE: 3
agctttgctt ctcaatttct tatttgcata atgagaaaaa aaggaaaatt aattttaaca    60
accaattcag tagttgattg agcaaatgcg ttgccaaaaa ggatgcttta gagacagtgt    120
tctctgcaca gataaggaca aacattattc agagggagtt tgtggatgga tcgtt         175

<210> SEQ ID NO 4
<211> LENGTH: 246
<212> TYPE: DNA
<213> ORGANISM: Artificial Sequence
<220> FEATURE:
<223> OTHER INFORMATION: Description of Artificial Sequence: Synthetic
      pAGE9 modified murine beta globin major promoter sequence

<400> SEQUENCE: 4
agctttgctt ctcaatttct tatttgcata atgagaaaaa aaggaaaatt aattttaaca    60
```

```
accaattcag tagttgattg agcaaatgcg ttgccaaaaa ggatgcttta gagacagtgt     120
tctctgcaca gataaggaca aacattattc agagggagta gggcaggagc cagggcagag     180
catataaggt gaggtaggat cagttgctcc tacatttgct tctgacatag ttgtggatgg     240
atcgtt                                                                246
```